(12) United States Patent
Mori et al.

(10) Patent No.: US 11,020,010 B2
(45) Date of Patent: Jun. 1, 2021

(54) BLOOD PRESSURE/PULSE WAVE MEASUREMENT DEVICE

(71) Applicant: Fukuda Denshi Co., Ltd., Tokyo (JP)

(72) Inventors: Naoki Mori, Kyoto (JP); Kazuhiro Matsui, Kyoto (JP)

(73) Assignee: FUKUDA DENSHI CO., LTD., Tokyo (JP)

( * ) Notice: Subject to any disclaimer, the term of this patent is extended or adjusted under 35 U.S.C. 154(b) by 171 days.

(21) Appl. No.: 16/084,986

(22) PCT Filed: Oct. 31, 2016

(86) PCT No.: PCT/JP2016/082321
§ 371 (c)(1),
(2) Date: Sep. 14, 2018

(87) PCT Pub. No.: WO2017/158909
PCT Pub. Date: Sep. 21, 2017

(65) Prior Publication Data
US 2019/0082980 A1   Mar. 21, 2019

(30) Foreign Application Priority Data
Mar. 16, 2016  (JP) .............................. JP2016-052605

(51) Int. Cl.
*A61B 5/021* (2006.01)
*A61B 5/0285* (2006.01)
(Continued)

(52) U.S. Cl.
CPC ...... *A61B 5/02116* (2013.01); *A61B 5/02007* (2013.01); *A61B 5/02028* (2013.01);
(Continued)

(58) Field of Classification Search
CPC ............ A61B 5/02116; A61B 5/02125; A61B 5/02141; A61B 5/0295
See application file for complete search history.

(56) References Cited

U.S. PATENT DOCUMENTS

| | | | |
|---|---|---|---|
| 6,355,000 | B1 | 3/2002 | Ogura |
| 2002/0133082 | A1 | 9/2002 | Ogura |

(Continued)

FOREIGN PATENT DOCUMENTS

| | | |
|---|---|---|
| CN | 1850000 A | 10/2006 |
| DE | 102007002951 A1 | 7/2008 |

(Continued)

OTHER PUBLICATIONS

Extended European Search Report for European Patent Application No. 16894526.9 dated Oct. 9, 2019, 7 pages.

(Continued)

*Primary Examiner* — Christine H Matthews
(74) *Attorney, Agent, or Firm* — Brundidge & Stanger, P.C.

(57) ABSTRACT

A blood pressure/pulse wave measurement device is provided with: first and second cuffs for pressing parts of the upper and lower limbs of a subject; and first and second tubing connected to the individual first and second cuffs. The blood pressure/pulse wave measurement device is additionally provided with: a first detection unit that is connected to the first cuffs via the first tubing and that detects a first pulse wave propagated through the first tubing; a second detection unit that is connected to the second cuffs via the second tubing and that detects a second pulse wave propagated through the second tubing; and a control unit that calculates the ankle brachial index and pulse wave velocity using the first and second pulse waves. The first detection unit and the control unit are accommodated within a first housing. The (Continued)

second detection unit is accommodated within a second housing.

4 Claims, 4 Drawing Sheets

(51) Int. Cl.
*A61B 5/02* (2006.01)
*A61B 5/022* (2006.01)
*A61B 5/026* (2006.01)
*A61B 5/0295* (2006.01)
*A61B 5/0235* (2006.01)

(52) U.S. Cl.
CPC ........ *A61B 5/0285* (2013.01); *A61B 5/02125* (2013.01); *A61B 5/02225* (2013.01); *A61B 5/0235* (2013.01); *A61B 5/0261* (2013.01); *A61B 5/0295* (2013.01); *A61B 5/02141* (2013.01); *A61B 2560/0443* (2013.01)

(56) References Cited

U.S. PATENT DOCUMENTS

| | | |
|---|---|---|
| 2006/0258944 A1 | 11/2006 | Takahashi |
| 2011/0230774 A1 | 9/2011 | Kobayashi et al. |
| 2012/0095353 A1 | 4/2012 | Mori et al. |

FOREIGN PATENT DOCUMENTS

| | | |
|---|---|---|
| JP | 2000-316821 A | 11/2000 |
| JP | 2003290160 A | 10/2003 |
| JP | 2004236730 A | 8/2004 |
| JP | 2013-144125 A | 7/2013 |
| JP | 2014-217707 A | 11/2014 |
| KR | 2002-0073374 A | 9/2002 |
| WO | 2010/035629 A1 | 4/2010 |

OTHER PUBLICATIONS

Examination Report from AU application No. 2016398146 dated Jun. 7, 2019, 5 pages.
International Search Report from International Application No. PCT/JP2016/082321 dated Jan. 10, 2017.

BLOOD PRESSURE/PULSE WAVE MEASUREMENT DEVICE

TECHNICAL FIELD

The present invention relates to a blood pressure pulse wave measurement apparatus.

BACKGROUND ART

Conventionally, a lower/upper limb blood pressure ratio (ABI) as an index representing clogging of blood vessels and a pulse wave velocity (PWV) as an index representing stiffness of blood vessels have been widely used for diagnosis of arteriosclerosis.

ABI and PWV each may be used solely, but for example, if arteriosclerosis generalizes, a measurement of only ABI may provide an ABI value within a normal range.

It is known that if the ABI value is normal, understanding a general progress of arteriosclerosis with PWV helps more accurate diagnosis.

Thus, to facilitate such diagnosis from various aspects, a measurement apparatus integrally including an ABI measurement apparatus and a PWV measurement apparatus, which have been conventionally separate, is recently on the market.

Conventionally, as this type of blood pressure pulse wave measurement apparatus, for example, as disclosed in PTL 1 (Japanese Patent Application Laid-Open No. 2000-316821), an apparatus is known in which four cuffs for the upper arms and ankles are connected to a main body and fitted around four limbs of a subject for measurement.

CITATION LIST

Patent Literature

PTL 1
Japanese Patent Application Laid-Open No. 2000-316821

SUMMARY OF INVENTION

Technical Problem

However, for the blood pressure pulse wave measurement apparatus described above, the cuffs for the upper arms and ankles have to be fitted around the upper arms and ankles of the subject by extending tubes from substantially the same location, and the plurality of tubes may get tangled, which requires much time and effort.

Thus, an object of the present invention is to provide a blood pressure pulse wave measurement apparatus that allows cuffs to be easily fitted around the upper arm and ankle of a subject without a plurality of tubes getting tangled.

Solution to Problem

In order to solve the above problem, a blood pressure pulse wave measurement apparatus of the present invention for measuring a lower/upper limb blood pressure ratio and a pulse wave velocity includes:

a first cuff for pressing part of an upper limb of a subject;
a second cuff for pressing part of a lower limb of the subject;
a first tube and a second tube connected to the first cuff and the second cuff, respectively;
a first detection section that is connected to the first cuff via the first tube and detects a first pulse wave propagating through the first tube;
a second detection section that is connected to the second cuff via the second tube and detects a second pulse wave propagating through the second tube; and
a control section that calculates an ankle brachial index and the pulse wave velocity using the first pulse wave and the second pulse wave, respectively,
in which the first detection section and the control section are disposed in a first casing, and the second detection section is disposed in a second casing.

The pulse wave velocity herein typically refers to brachial-ankle pulse wave velocity baPWV and heart-ankle pulse wave velocity haPWV. Cardio ankle vascular index (CAVI) that is an index reflecting arterial stiffness from the heart to ankle can be calculated by correcting heart-ankle pulse wave velocity haPWV with a logarithmic pulse wave. The lower/upper limb blood pressure ratio typically refers to ankle brachial index ABI.

In the blood pressure pulse wave measurement apparatus of the present invention, the first casing to which the cuff for the upper arm is connected and the second casing to which the cuff for the ankle is connected are separated. Thus, when the cuffs for the upper arm and ankle are fitted around the upper arm and ankle of the subject, the second casing can be disposed near the ankle. Then, the cuffs can be easily fitted around four limbs of the subject without the tube connected to the cuff for the upper arm and the tube connected to the cuff for the ankle getting tangled.

In the blood pressure pulse wave measurement apparatus of an embodiment, the first detection section includes:

a first pressure pump that feeds air through the first tube into the first cuff and pressurizes the first cuff; and
a first pressure sensor that detects a pulse wave propagating through the first tube, and
in which the second detection section includes:
a second pressure pump that feeds air through the second tube into the second cuff and pressurizes the second cuff; and
a second pressure sensor that detects a pulse wave propagating through the second tube.

In the blood pressure pulse wave measurement apparatus of the present invention, the first casing to which the cuff for the upper arm is connected and the second casing to which the cuff for the ankle is connected are separated. Then, the length of the first tube and the length of the second tube may be adjusted to be substantially the same. Thus, timing of detection of a pulse wave in the upper arm and timing of detection of a pulse wave in the ankle can be substantially the same, thereby improving measurement accuracy of ABI and PWV.

In the blood pressure pulse wave measurement apparatus of an embodiment, wherein the control section calculates a blood pressure value of the subject based on the first pulse wave.

In the blood pressure pulse wave measurement apparatus of the present invention, the first casing to which the cuff for the upper arm is connected and the second casing to which the cuff for the ankle is connected are separated. Thus, when blood pressure only of the subject is measured, the cuff for the upper arm only may be fitted around the upper arm of the subject to measure the blood pressure.

In the blood pressure pulse wave measurement apparatus of an embodiment, the pulse wave velocity includes a brachial-ankle pulse wave velocity baPWV and a heart-ankle pulse wave velocity haPWV, and the control section calculates a cardio ankle vascular index (CAVI) by correcting the heart-ankle pulse wave velocity haPWV with a logarithmic pulse wave.

In the blood pressure pulse wave measurement apparatus of the present invention, the cardio ankle vascular index can be calculated based on the heart-ankle pulse wave velocity haPWV.

Advantageous Effects of Invention

As is apparent from the above, the blood pressure pulse wave measurement apparatus of the present invention allows the cuffs to be easily fitted around the upper arm and ankle of the subject.

DESCRIPTION OF EMBODIMENTS

Figure 1:
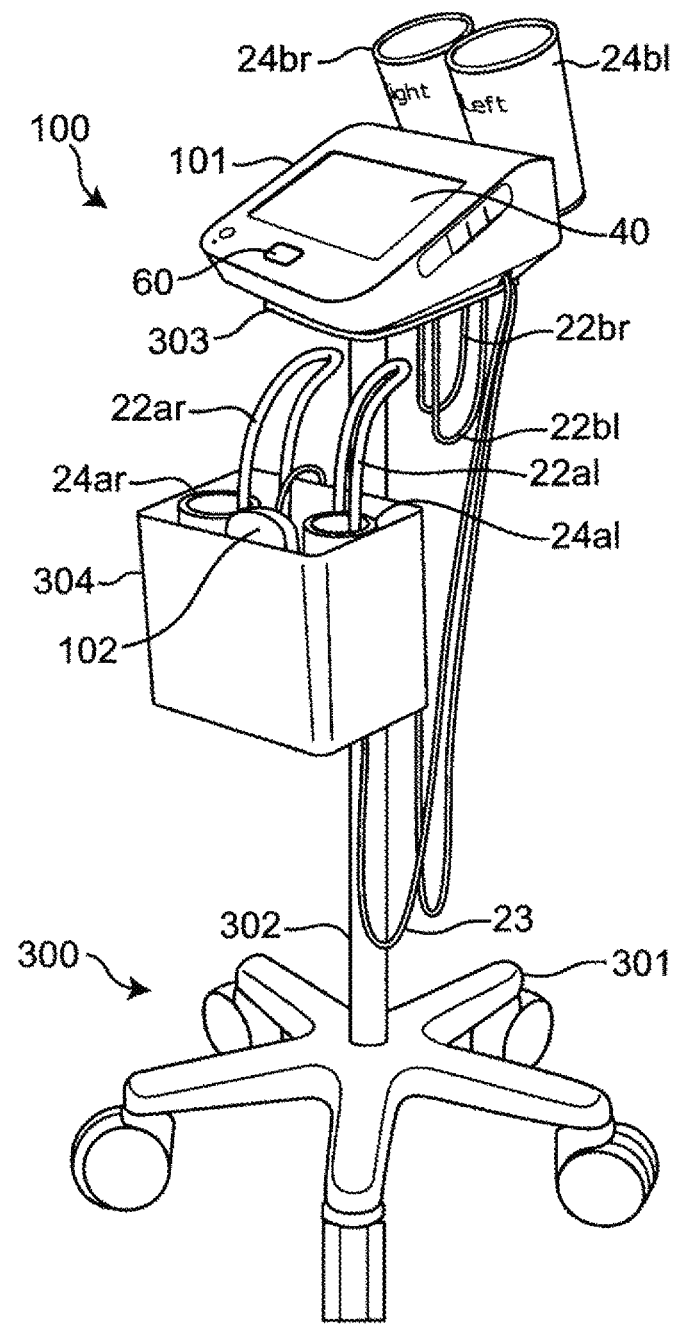
FIG. 1 is a perspective view of blood pressure pulse wave measurement apparatus 100 according to an embodiment of the present invention being housed in housing wagon 300.

Embodiments of the present invention will be described with reference to the accompanying drawings. In the embodiments below, like components are denoted by like reference numerals, and descriptions thereof are omitted.

FIG. 1 is a perspective view of blood pressure pulse wave measurement apparatus 100 according to an embodiment of the present invention being housed in housing wagon 300. Blood pressure pulse wave measurement apparatus 100 includes main unit 101 as a first casing, ankle unit 102 as a second casing, and four cuffs 24*ar*, 24*al*, 24*br*, 24*b*1. Housing wagon 300 includes leg 301 with casters, post 302 standing on leg 301, placing table 303 mounted to an end of post 302, and housing box 304 mounted in the middle of post 302 and opening upward. On placing table 303, main unit 101 is placed. In housing box 304, ankle unit 102 and cuffs 24*ar*, 24*a*1 for the right ankle (right lower limb) and left ankle (left upper limb) as a second cuff are housed. Cuffs 24*br*, 24*bl* for the right upper arm (right upper limb) and left upper arm (left upper limb) as a first cuff are hung and held on hooks 101*e*, 101*f* (shown in FIG. 2) provided in the rear of main unit 101.

Ankle unit 102 and cuffs 24*ar*, 24*a*1 for the right ankle (right lower limb) and left ankle (left upper limb) are connected by tubes 22*ar*, 22*a*1 as second tube through which air for pressurizing the cuffs is passed. Similarly, main unit 101 and cuffs 24*br*, 24*bl* for the right upper arm (right upper limb) and left upper arm (left upper limb) are connected by tubes 22*br*, 22*bl* as a first tube through which air for pressurizing the cuffs is passed. Main unit 101 is connected to ankle unit 102 by connection cable 23 so as to be able to supply power and communicate.

Figure 2:
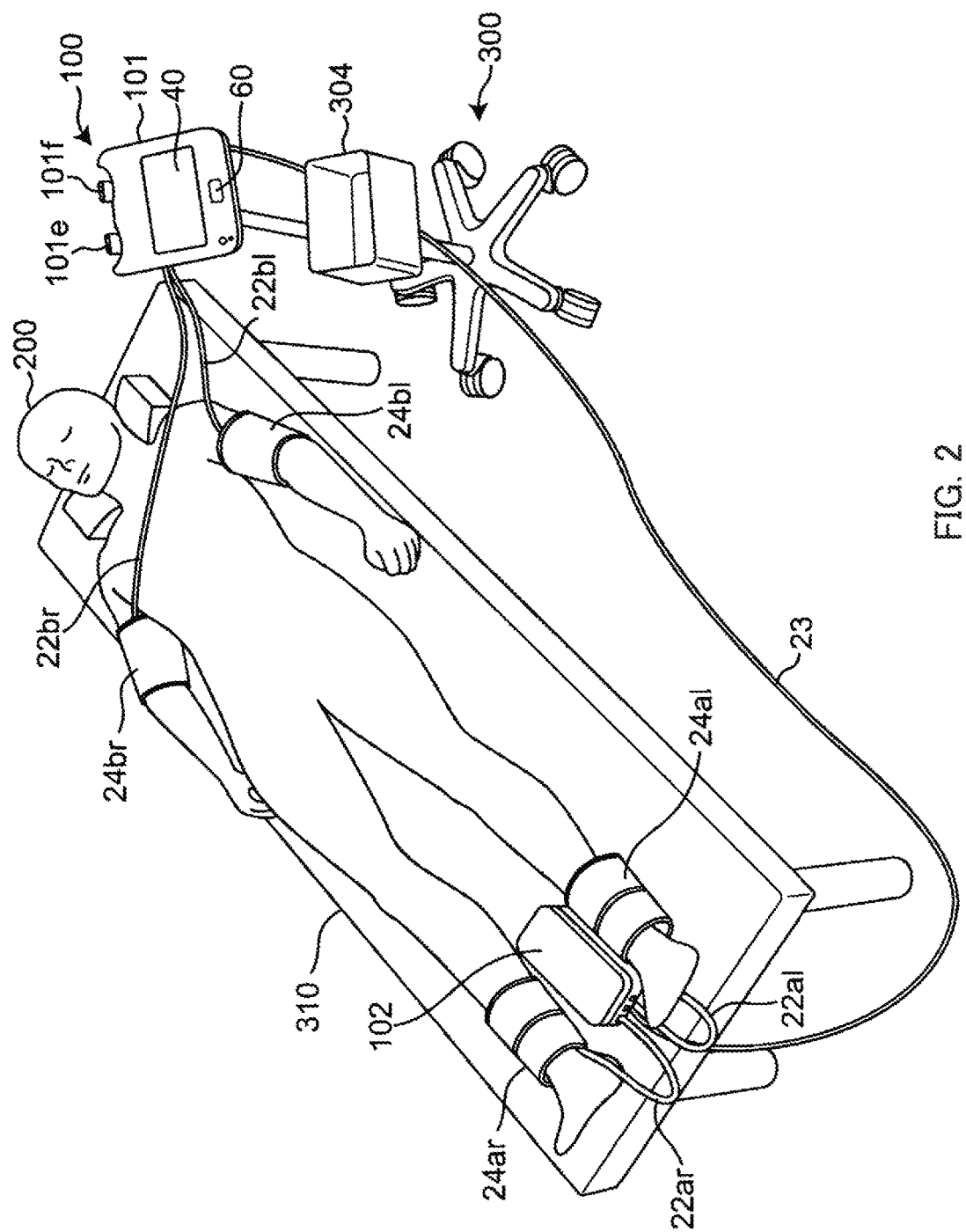
FIG. 2 is a perspective view of blood pressure pulse wave measurement apparatus 100 in FIG. 1 being used.

FIG. 2 is a perspective view of blood pressure pulse wave measurement apparatus 100 in FIG. 1 being used. As shown in FIG. 2, subject 200 is lying on his/her back on bed 310. Ankle unit 102 is taken out of housing box 304, and placed between the right ankle and left ankle of subject 200 on bed 310.

Cuffs 24*ar*, 24*al*, 24*br*, 24*bl* are fitted around the limbs of subject 200. Specifically, cuffs 24*ar*, 24*al*, 24*br*, 24*bl* are fitted around the right ankle (right lower limb), left ankle (left upper limb), right upper arm (right upper limb), and left upper arm (left upper limb), respectively.

As described above, main unit 101 to which cuffs 24*br*, 24*bl* for the upper arms are connected and ankle unit 102 to which cuffs 24*ar*, 24*a*1 for the ankles are connected are separated. Thus, when cuffs 24*br*, 24*bl*, 24*ar*, 24*a*1 for the upper arms and ankles are fitted around the upper arms and ankles of subject 200, ankle unit 102 can be disposed near the ankles. Then, the cuffs can be easily fitted around four limbs of subject 200 without tubes 22*br*, 22*bl* connected to cuffs 24*br*, 24*bl* for the upper arms and tubes 22*ar*, 22*a*1 connected to cuffs 24*ar*, 24*a*1 for the ankles getting tangled.

An example of the cuffs being fitted only around the right ankle, left ankle, right upper arm, and left upper arm are described below. However, the "limbs" refer to sites included in four limbs, and may include the wrist, fingertip, or the like. Cuffs 24*ar*, 24*al*, 24*br*, 24*bl* are collectively called "cuff 24" unless there is a need to make a distinction.

Figure 3:
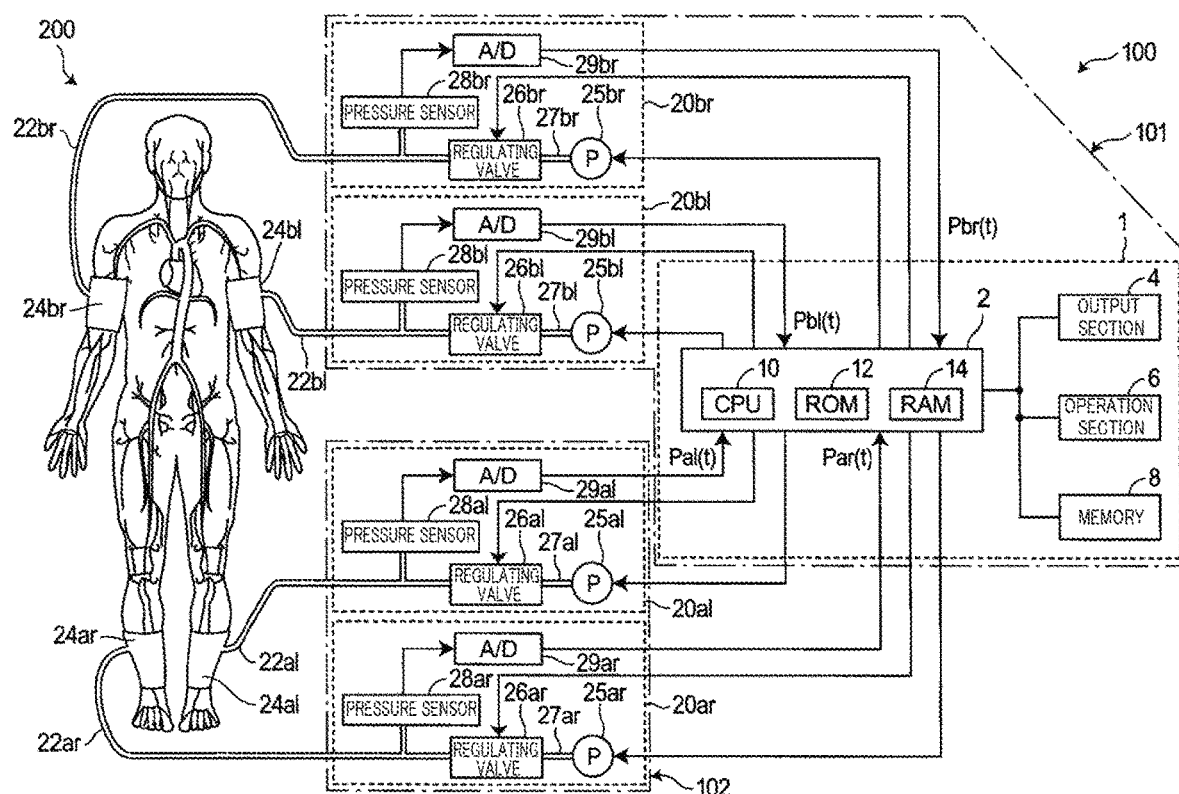
FIG. 3 is a schematic block diagram of a configuration of a control system in blood pressure pulse wave measurement apparatus 100 in FIG. 1.

FIG. 3 is a schematic block diagram of a configuration of a control system in blood pressure pulse wave measurement apparatus 100 in FIG. 1. As shown in FIG. 3, ankle unit 102 includes two detection units 20*ar*, 20*a*1 as a second detection section. Main unit 101 includes information processing unit 1 and two detection units 20*br*, 20*bl* as a first detection section.

Detection units 20*ar*, 20*al*, 20*br*, 20*bl* each include hardware required for detecting a pulse wave in the limbs of subject 200. Detection units 20*ar*, 20*al*, 20*br*, 20*b*1 may all have the same configuration, and thus are collectively called "detection unit 20" unless there is a need to make a distinction.

Information processing unit 1 includes control section 2, output section 4, operation section 6, and memory 8.

Control section 2 controls entire blood pressure pulse wave measurement apparatus 100, and is constituted by a computer typically including central processing unit (CPU) 10, read only memory (ROM) 12, and random access memory (RAM) 14.

CPU 10 corresponds to an arithmetic processing section, reads a program previously stored in ROM 12, and executes the program using RAM 14 as a work memory.

Output section 4, operation section 6, and memory 8 are connected to control section 2. Output section 4 outputs a measured pulse wave, analysis results of the pulse wave, or the like. Output section 4 may be a display device constituted by a light emitting diode (LED), a liquid crystal display (LCD), or the like, or may be a printer (driver). In this example, as shown in FIGS. 1 and 2, display screen 40 of an LCD is provided as output section 4 on an upper surface of main unit 101.

Operation section 6 shown in FIG. 3 receives an instruction from a user. In this example, as shown in FIGS. 1 and 2, operation switch 60 is provided as operation section 6 on the upper surface of main unit 101. The user can use operation switch 60 to input instructions to power on/off, start blood pressure measurement, or the like.

Memory 8 shown in FIG. 3 holds various data or programs. CPU 10 of control section 2 reads or writes the data or programs recorded in memory 8. Memory 8 may be constituted by, for example, a hard disk, non-volatile memory (for example, flush memory), removable external recording medium, or the like.

Next, a configuration of each detection unit 20 will be described in detail.

Detection unit 20br is connected to cuff 24br via tube 22br, and detects a pulse wave propagating through tube 22br. Specifically, detection unit 20br adjusts and detects internal pressure of cuff 24br (hereinafter referred to as "cuff pressure") fitted around the right upper arm of subject 200 to detect a pulse wave in the right upper arm. Cuff 24br includes therein a fluid bag (an air bag in this example) (not shown).

Detection unit 20br includes pressure sensor 28br as a first pressure sensor, regulating valve 26br, pressure pump 25br as a first pressure pump, analog to digital (A/D) converter 29br, and tube 27br. Cuff drive section 31br feeds air through tube 22br into cuff 24br and pressurizes cuff 24br. Cuff 24br, pressure sensor 28br, and regulating valve 26br are connected by tube 22br.

Pressure sensor 28br detects pressure fluctuations transmitted through tube 22br, and includes, as an example, a plurality of sensor elements arranged at regular intervals on a semiconductor chip of single crystal silicon or the like. A pressure fluctuation signal detected by pressure sensor 28br is converted into a digital signal by A/D converter 29br and input as pulse wave signal pbr(t) to control section 2.

Regulating valve 26br is interposed between pressure pump 25br and cuff 24br, and maintains pressure used for pressurizing cuff 24br within a predetermined range during measurement. Pressure pump 25br is actuated according to a detection instruction from control section 2, and supplies air to the fluid bag (not shown) in cuff 24br to pressurize cuff 24br.

The pressurization presses cuff 24br against a measurement site, and pressure changes according to the pulse wave in the right upper arm are transmitted through tube 22br to detection unit 20br. Detection unit 20br detects the transmitted pressure changes to detect the pulse wave in the right upper arm.

Detection unit 20bl similarly includes pressure sensor 28bl as a first pressure sensor, regulating valve 26bl, pressure pump 25bl as a first pressure pump, A/D converter 29bl, and tube 27b1. Cuff 24bl, pressure sensor 28bl, and regulating valve 26bl are connected by tube 22b1. Pressure sensors 28br, 28bl as the first pressure sensor detect a pulse wave (first pulse wave) propagating through tubes 22br, 22bl, respectively.

Detection unit 20ar includes pressure sensor 28ar as a second pressure sensor, regulating valve 26ar, pressure pump 25ar as a second pressure pump, A/D converter 29ar, and tube 27ar. Cuff 24ar, pressure sensor 28ar, and regulating valve 26ar are connected by tube 22ar.

Detection unit 20a1 similarly includes pressure sensor 28a1 as a second pressure sensor, regulating valve 26al, pressure pump 25a1 as a second pressure pump, A/D converter 29al, and tube 27a1. Cuff 24al, pressure sensor 28al, and regulating valve 26a1 are connected by tube 22a1. Pressure sensors 28ar, 28a1 as the second pressure sensor detect a pulse wave (second pulse wave) propagating through tubes 22ar, 22al, respectively.

Functions of components in detection units 20bl, 20ar, 20a1 are the same as those in detection unit 20br, and thus detailed descriptions will not be repeated. Also, components in detection unit 20 will be described without symbols such as "ar" or "br" unless there is a need to make a distinction.

When the length of tubes 22br, 22bl and the length of tubes 22ar, 22a1 are different, a delay may occur between timing of detection of a pulse wave in the upper arm and timing of detection of a pulse wave in the ankle, which causes an error in measurement accuracy of ABI and PWV. On the other hand, in blood pressure pulse wave measurement apparatus 100, main unit 101 to which cuffs 24br, 24bl for the upper arms are connected and ankle unit 102 to which cuffs 24ar, 24a1 for the ankles are connected are separated, and thus the length of tubes 22br, 22bl and the length of tubes 22ar, 22a1 may be adjusted to be substantially the same. Thus, timing of detection of a pulse wave in the upper arm and timing of detection of a pulse wave in the ankle can be substantially the same, thereby improving measurement accuracy of ABI and PWV.

Blood pressure pulse wave measurement apparatus 100 measures a blood pressure value by a known oscillometric method using control with control section 2 (particularly CPU 10) as shown in a process flow in FIG. 4 described later. Also, blood pressure pulse wave measurement apparatus 100 detects a pulse wave to obtain brachial-ankle pulse wave velocity baPWV and heart-ankle pulse wave velocity haPWV as pulse wave velocities, and obtain ankle brachial index ABI as a lower/upper limb blood pressure ratio. Specifically, control section 2 calculates ankle brachial index (ABI) and pulse wave velocity (PWV) using a pulse wave detected by detection units 20br, 20bl, 20al, 20ar. Control section 2 also calculates a blood pressure value of the subject using the pulse wave detected by 20br, 20b1. Further, control section 2 calculates an index such as cardio ankle vascular index (CAVI) calculated based on heart-ankle pulse wave velocity haPWV. Control section 2 calculates CAVI by correcting heart-ankle pulse wave velocity haPWV with a logarithmic pulse wave. As known, brachial-ankle pulse wave velocity baPWV and heart-ankle pulse wave velocity haPWV are indexes representing stiffness of blood vessels, and ankle brachial index ABI is an index representing clogging of blood vessels.

An operation of blood pressure pulse wave measurement apparatus 100 configured as described above will be now described.

Figure 4:
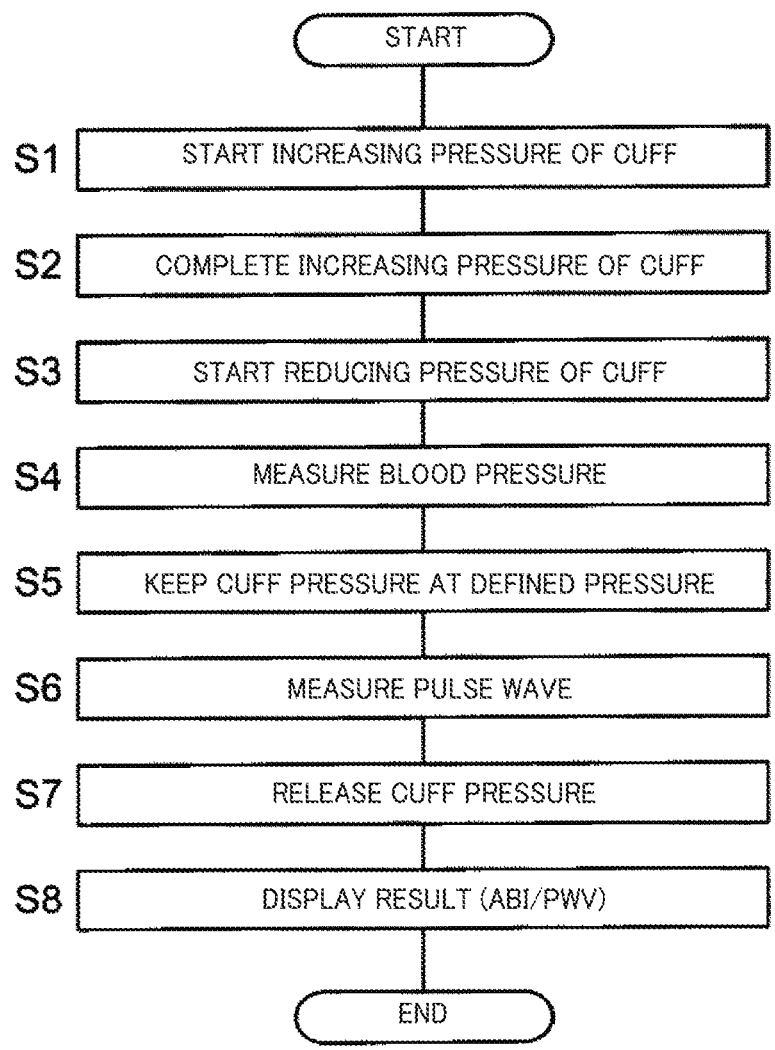
FIG. 4 is a flowchart of processing for measuring a lower/upper limb blood pressure ratio and a pulse wave velocity performed by blood pressure pulse wave measurement apparatus 100 in FIG. 1.

FIG. 4 is a flowchart of processing for measuring a lower/upper limb blood pressure ratio and a pulse wave velocity performed by blood pressure pulse wave measurement apparatus 100 in FIG. 1. Specifically, when the measurement is started, as shown in step S1 in FIG. 4, pump 25 in each detection unit 20 is driven to start increasing pressure of each cuff 24.

Then, as shown in step S2, with pressure sensor 28 monitoring cuff pressure, the cuff pressure is increased to predetermined pressure (pressure higher than maximum blood pressure of subject 200) to stop pump 25 (COMPLETE INCREASING PRESSURE OF CUFF). Then, as shown in step S3, regulating valve 26 is controlled to start reducing pressure of each cuff 24 to gradually reduce the cuff pressure. In the pressure reducing process, fluctuations in arterial volume that occur in the artery of the measurement site are detected as a pulse wave signal by pressure sensor 28 via each cuff 24.

Then, as shown in step S4, based on an amplitude of the pulse wave signal, a predetermined algorithm by the known oscillometric method is used to calculate maximum blood pressure (systolic blood pressure) and minimum blood pressure (diastolic blood pressure) (MEASURE BLOOD PRESSURE). In addition, CPU 10 serves as a lower/upper limb blood pressure ratio obtaining section to calculate ankle brachial index ABI=(ankle systolic blood pressure)/(brachial systolic blood pressure) for each of the left and right sides of the body of subject 200. In this example, a pulse (in beats per minute) is also calculated. The blood pressure may be calculated in the pressure increasing process, not limited to the pressure reducing process.

Next, as shown in step S5, regulating valve 26 is closed to keep the cuff pressure at defined pressure (for example, about 50 mmHg). In this state, as shown in step S6, CPU 10 serves as a pulse wave velocity obtaining section to obtain a pulse wave velocity that is an index representing stiffness of blood vessels of the subject based on a pulse wave measured by pressure sensor 28.

Once the measurement is completed, as shown in step S7 in FIG. 4, regulating valve 26 is fully opened to release the cuff pressure. Then, as shown in step S8, CPU 10 serves as a display processing section to display a measurement result on display screen 40 (see FIG. 2) provided on the upper surface of main unit 101.

In this embodiment, the configuration in which pressure sensor 28 is used to detect a pulse wave has been described, however, an arterial volume sensor (not shown) may be used to detect a pulse wave. In this case, the arterial volume sensor may include, for example, a light emitting element that emits light to the artery, and a light receiving element that receives the light emitted by the light emitting element and transmitted through or reflected by the artery. Alternatively, the arterial volume sensor may include a plurality of electrodes, pass a certain minute electric current through a measurement site of subject 200, and detect changes in voltage caused by changes in impedance resulting from propagation of a pulse wave (bioimpedance).

The embodiments described above are illustrative and various modifications may be made without departing from the scope of the present invention. The embodiments described above may stand solely, but may be combined with each other. Various features in different embodiments may also stand solely, but the features in the different embodiments may be combined with each other.

REFERENCE SIGNS LIST 1 information processing unit
2 control section
4 output section
6 operation section
8 memory
10 CPU
12 ROM
14 RAM
20*ar*, 20*al*, 20*br*, 20*bl* detection unit
22*ar*, 22*al*, 22*br*, 22*bl*, 27*ar*, 27*al*, 27*br*, 27*bl* tube
23 connection cable
24*ar*, 24*al*, 24*br*, 24*bl* cuff
25*ar*, 25*al*, 25*br*, 25*bl* pressure pump
26*ar*, 26*al*, 26*br*, 26*bl* regulating valve
28*ar*, 28*al*, 28*br*, 28*bl* pressure sensor
29*ar*, 29*al*, 29*br*, 29*bl* A/D converter
40 display screen
60 operation switch
100 blood pressure pulse wave measurement apparatus
101 main unit
101*e*, 101*f* hook
102 ankle unit
200 subject
300 housing wagon
301 leg
302 post
303 placing table
304 housing box

The invention claimed is:

1. A blood pressure pulse wave measurement apparatus for measuring a lower/upper limb blood pressure ratio and a pulse wave velocity, the apparatus comprising:
  a pair of first cuffs for pressing part of upper limbs of a subject;
  a pair of second cuffs for pressing part of lower limbs of the subject;
  a pair of first tubes and a pair of second tubes connected to the pair of first cuffs and the pair of second cuffs, respectively;
  a first detection circuitry that is connected to the pair of first cuffs via the pair of first tubes and detects a first pulse wave propagating through the pair of first tubes;
  a second detection circuitry that is connected to the pair of second cuffs via the pair of second tubes and detects a second pulse wave propagating through the pair of second tubes; and
  a control circuitry that calculates an ankle brachial index and the pulse wave velocity using the first pulse wave and the second pulse wave, respectively,
  wherein the first detection circuitry and the control circuitry are disposed in a first casing, and the second detection circuitry is disposed in a second casing, and
  wherein the pair of first tubes and the pair of second tubes are configured to be adjusted to be substantially the same in length such that a timing of detection of the first pulse wave and a timing of detection of the second pulse wave are substantially the same.

2. The blood pressure pulse wave measurement apparatus according to claim 1, wherein the first detection circuitry includes:
  a pair of first pressure pumps that feeds air through the pair of first tubes into the pair of first and pressurizes the pair of first cuffs; and
  a pair of first pressure sensors that detect pulse waves propagating through the pair of first tubes, and
wherein each of the second detection circuitry includes:
  a pair of second pressure pumps that feeds air through the pair of second tubes into the pair of second cuffs and pressurizes the pair of second cuffs; and
  a pair of second pressure sensors that detect pulse waves propagating through the pair of second tubes.

3. The blood pressure pulse wave measurement apparatus according to claim 1 or 2, wherein the control circuitry calculates a blood pressure value of the subject based on the first pulse wave.

4. The blood pressure pulse wave measurement apparatus according to claim 1, wherein the pulse wave velocity includes a brachial-ankle pulse wave velocity and a heart-ankle pulse wave velocity, and
  the control circuitry calculates a cardio ankle vascular index based on the heart-ankle pulse wave velocity.

* * * * *